United States Patent
Shirai et al.

(10) Patent No.: US 7,250,537 B2
(45) Date of Patent: Jul. 31, 2007

(54) METHOD OF HYDROGENATING PHENOL

(75) Inventors: Masayuki Shirai, Miyagi (JP);
Chandrashekhar Vasant Rode, Pune (IN); Uday Dattopant Joshi, Nanded (IN); Kazuo Torii, Miyagi (JP); Takafumi Sato, Miyagi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/553,792

(22) PCT Filed: Mar. 30, 2004

(86) PCT No.: PCT/JP2004/004499

§ 371 (c)(1),
(2), (4) Date: Oct. 18, 2005

(87) PCT Pub. No.: WO2004/094352

PCT Pub. Date: Nov. 4, 2004

(65) Prior Publication Data

US 2006/0194989 A1 Aug. 31, 2006

(30) Foreign Application Priority Data

Apr. 18, 2003 (JP) ............................. 2003-115094
Aug. 22, 2003 (JP) ............................. 2003-299181
Dec. 18, 2003 (JP) ............................. 2003-421700

(51) Int. Cl.
*C07C 45/00* (2006.01)
*C07C 27/00* (2006.01)
*C07C 29/00* (2006.01)

(52) U.S. Cl. ..................... 568/342; 568/362; 568/830; 568/835

(58) Field of Classification Search ............... None
See application file for complete search history.

(56) References Cited

U.S. PATENT DOCUMENTS 3,177,258 A * 4/1965 Koch, Jr. et al. ........... 568/579
5,107,038 A * 4/1992 Weinstein .................. 568/834
6,002,047 A * 12/1999 Jansen et al. .............. 568/395

FOREIGN PATENT DOCUMENTS

| JP | 3-173842 | 7/1991 |
|---|---|---|
| JP | 10-168021 | 6/1998 |
| JP | 11-315037 | 11/1999 |
| JP | 2000-117104 | 4/2000 |
| JP | 2000-508653 | 7/2000 |
| JP | 2002-186854 | 7/2002 |

OTHER PUBLICATIONS

Sekiyu Kagaku Purosesu ("Petrochemical Processes"), edited by the Japan Petroleum Institute, Kodansha, pp. 144-148 2001.
Nagendranath Mahata et al., "Influence of palladium precursors on structural properties and phenol hydrogenation characteristics of supported palladium catalysts", Journal of Catalysis, vol. 196, pp. 262-270 2000.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

The present invention provides a novel method of hydrogenating a phenol for hydrogenating a phenol industrially advantageously. The present invention relates, in the case of phenol hydrogenation in which carbon dioxide is made to participate in the reaction, to a method of hydrogenating a phenol characterized by using a supported rhodium and/or ruthenium catalyst, whereby the phenol is hydrogenated efficiently at a lower reaction temperature than with prior art; such a method characterized in that carbon dioxide having a temperature of 20 to 250° C. and a pressure of 0.1 to 50 MPa is used as the carbon dioxide; and such a method characterized in that hydrogen under conditions of a temperature of 20 to 250° C. and a pressure of 0.1 to 50 MPa is used.

An environmentally friendly phenol hydrogenation process that uses no harmful organic solvents can be realized.

16 Claims, No Drawings

METHOD OF HYDROGENATING PHENOL

TECHNICAL FIELD

The present invention relates to a novel method of hydrogenating a phenol that enables an industrially important phenol hydrogenation process to be carried out as an environmentally friendly process that uses no harmful organic solvents, and more specifically relates, for example, to a method of efficiently hydrogenating a phenol using carbon dioxide such as supercritical carbon dioxide and a highly active supported rhodium and/or ruthenium catalyst at a lower reaction temperature than with prior art and while preventing a drop in activity of the catalyst. The present invention provides, in the field of phenol hydrogenation product manufacturing art using a phenol hydrogenation process, a novel manufacturing technique in which a supported rhodium and/or ruthenium catalyst and carbon dioxide are made to participate in the reaction, whereby the phenol hydrogenation can be made to proceed highly efficiently at a low reaction temperature. For example, cyclohexanone and cyclohexanol, which are obtained through the hydrogenation of the phenol are industrially very important as raw materials of adipic acid and $\epsilon$-caprolactam. The present invention is useful as an invention that provides a novel method of hydrogenating a phenol that enables such industrially important substances to be produced efficiently, and moreover enables problems of conventional phenol hydrogenation processes to be thoroughly resolved.

BACKGROUND ART

Adipic acid, which is a raw material of 66-nylon, and $\epsilon$-caprolactam, which is a raw material of 6-nylon, are manufactured on a worldwide scale in amounts of 2.2 million tons and 3.7 million tons per year respectively.

Adipic acid is obtained industrially by oxidizing cyclohexanone, cyclohexanol, or a mixture thereof with nitric acid. $\epsilon$-caprolactam, on the other hand, is obtained through a rearrangement reaction of cyclohexanone oxime that has been obtained by converting cyclohexanone into the oxime. Moreover, KA oil, which contains cyclohexanone and cyclohexanol is manufactured through a cyclohexane oxidation process or a phenol hydrogenation process, and it has been reported that the amount of KA oil produced per year is 5 million tons (*Sekiyu Kagaku Purosesu* ("Petrochemical Processes"), edited by the Japan Petroleum Institute, Kodansha, pages 144-148 (2001)).

However, out of these processes, with the cyclohexane oxidation process, approximately 20% of higher oxides are produced, and the handling thereof is problematic. On the other hand, with the phenol hydrogenation process, KA oil has been obtained through a vapor phase method using a supported palladium catalyst by reacting a phenol or the like in a temperature range of 130 to 180° C. so as to hydrogenate the benzene ring of the phenol (N. Mahata and V. Vishwanathan, Journal of Catalysis, 196, 262-270 (2000)). This method of hydrogenating phenol has the drawback that the reaction temperature is high, and hence the catalyst is prone to being deactivated through accumulation of carbonaceous matter on the surface thereof during the reaction; making the reaction proceed at a lower temperature has thus become an issue. Moreover, there has been proposed a method of synthesizing 3-methylcyclohexanone and 3-methylcyclohexanol from meta-cresol through hydrogenation using carbon dioxide and a 5% palladium catalyst under reaction conditions of 250 to 400° C. and a ($CO_2+H_2$) pressure of 120 bar (Published Japanese Translation of PCT Application No. 2000-508653) However, with this type of hydrogenation method, drawbacks have been observed in that deoxygenation and functional group breakaway occur so as to produce unwanted byproducts such as methylcyclohexane and toluene. Moreover, the supported metal of the catalyst used in such a hydrogenation method is limited to palladium, and hence it has been difficult to reduce the reaction temperature, or improve properties such as the activity and selectivity; there have thus been calls for the development of a new highly active metal catalyst.

DISCLOSURE OF THE INVENTION

As described above, with a conventional phenol hydrogenation process, the reaction temperature is high, and hence there are drawbacks such as the catalyst activity being prone to dropping or unwanted byproducts being obtained; it has thus been desired to reduce the reaction temperature. Moreover, with the conventional phenol hydrogenation process, the metal used in the catalyst is limited to palladium, and hence there has been the drawback that it is difficult to make further progress in reaction control with regard to selectivity and so on. Amid this state of affairs, and in view of the prior art described above, the present inventors have carried out assiduous studies over many years aimed at thoroughly resolving these problems, and as a result have accomplished the present invention upon discovering that by making a supported rhodium and/or ruthenium catalyst and carbon dioxide participate in the reaction, the reaction temperature can be reduced, and moreover the phenol hydrogenation can be made to proceed highly efficiently.

It is an object of the present invention to provide a novel method of hydrogenating a phenol, which uses carbon dioxide and a supported rhodium and/or ruthenium catalyst, and enables the phenol to be hydrogenated efficiently.

Moreover, it is an object of the present invention to provide a method of manufacturing compounds such as cyclohexanone and cyclohexanol highly efficiently at a low reaction temperature through such a phenol hydrogenation process.

To attain the above objects, the present invention is constituted from the following technical means.

(1) A method of hydrogenating a phenol using carbon dioxide, the method characterized by reacting a phenol and hydrogen together in the presence of a supported rhodium and/or ruthenium catalyst using carbon dioxide so as to hydrogenate the phenol.

(2) The method of hydrogenating a phenol according to above item (1), characterized in that the hydrogenation is carried out at a reaction temperature of 20 to 250° C.

(3) The method of hydrogenating a phenol according to above item (1) or (2), characterized in that the hydrogenation is carried out at a reaction pressure of 0.2 to 100 MPa.

(4) The method of hydrogenating a phenol according to any of above items (1) through (3), characterized in that at least one type of supported catalyst selected from an activated charcoal-supported rhodium catalyst, an alumina-supported rhodium catalyst and an activated charcoal-supported ruthenium catalyst is used as the catalyst.

(5) The method of hydrogenating a phenol according to any of above items (1) through (4), characterized in that carbon dioxide having a temperature of 20 to 250° C. and a pressure of 0.1 to 50 MPa is used as the carbon dioxide.

(6) The method of hydrogenating a phenol according to any of above items (1) through (5), characterized in that hydrogen under conditions of a temperature of 20 to 250° C. and a pressure of 0.1 to 50 MPa is used.

(7) The method of hydrogenating a phenol according to any of above items (1) through (6), characterized in that supercritical carbon dioxide is used as the carbon dioxide.

(8) The method of hydrogenating a phenol according to any of above items (1) through (7), characterized in that the hydrogen pressure and the carbon dioxide pressure are adjusted in the presence of the phenol so as to control the conversion ratio of the phenol and/or the selectivities for the phenol hydrogenation products.

(9) The method of hydrogenating a phenol according to any of above items (1) through (8), characterized in that the hydrogen pressure and the carbon dioxide pressure are adjusted in the absence of the phenol so as to hydrogenate a cyclohexanone derivative and control the selectivities for the phenol hydrogenation products.

(10) The method of hydrogenating a phenol according to any of above items (1) through (9), characterized in that after the conversion ratio of the phenol has reached 100%, the hydrogen pressure and the carbon dioxide pressure are adjusted so as to control the selectivities for the phenol hydrogenation products.

(11) The method of hydrogenating a phenol according to any of above items (1) through (10), characterized in that phenol or cresol is used as the phenol.

(12) The method of hydrogenating a phenol according to above item (11), characterized in that cresol comprising at least one of meta-cresol, ortho-cresol and para-cresol is used as the cresol.

(13) The method of hydrogenating a phenol according to any of above items (1) through (10), characterized in that naphthol is used as the phenol.

(14) The method of hydrogenating a phenol according to any of above items (1) through (13), characterized in that each of the phenol hydrogenation products is a cyclohexanone derivative or a cyclohexanol derivative.

(15) The method of hydrogenating a phenol according to above item (14), characterized in that the cyclohexanone derivative is cyclohexanone, meta-methylcyclohexanone, ortho-methylcyclohexanone, para-methylcyclohexanone or tetralone, and the cyclohexanol derivative is cyclohexanol, meta-methylcyclohexanol, ortho-methylcyclohexanol, para-methylcyclohexanol, 1,2,3,4-tetrahydronaphthol, 5,6,7,8-tetrahydronaphthol or decahydronaphthol.

(16) A method of hydrogenating a cyclohexanone derivative using carbon dioxide, the method characterized by reacting a cyclohexanone derivative and hydrogen together in the presence of a supported rhodium and/or ruthenium catalyst using carbon dioxide at a reaction temperature of 20 to 250° C. and a reaction pressure of 0.2 to 100 MPa so as to hydrogenate the cyclohexanone derivative.

(17) The method of hydrogenating a cyclohexanone derivative according to above item (16), characterized in that the hydrogen pressure and the carbon dioxide pressure are adjusted in the absence of a phenol so as to control the selectivity for a cyclohexanol derivative.

(18) The method of hydrogenating a cyclohexanone derivative according to above item (16) or (17), characterized in that the cyclohexanone derivative is cyclohexanone, meta-methylcyclohexanone, ortho-methylcyclohexanone, para-methylcyclohexanone or tetralone, and the cyclohexanol derivative is cyclohexanol, meta-methylcyclohexanol, ortho-methylcyclohexanol, para-methylcyclohexanol, 1,2,3,4-tetrahydronaphthol, 5,6,7,8-tetrahydronaphthol or decahydronaphthol.

The present invention will now be described in more detail.

To facilitate description of the present invention, in the following a detailed description will be given taking as an example the case of hydrogenating a phenol by introducing the phenol, hydrogen, carbon dioxide and an activated charcoal-supported rhodium catalyst into a reactor of internal volume 50 ml set to a reaction temperature of 80° C.

The method of hydrogenating a phenol of the present invention, which has been developed by the present inventors through various experiments, is a method of hydrogenating a phenol in which, for example, the phenol and hydrogen are reacted together for approximately 2 hours using carbon dioxide and a supported rhodium and/or ruthenium catalyst in a reactor at a reaction temperature of 80° C., whereby the phenol can be hydrogenated to synthesize cyclohexanone and cyclohexanol at a lower reaction temperature than conventionally.

Preferable examples of the phenol used as the substrate, i.e. the raw material, in the present invention are aromatic hydroxy compounds in which a hydrogen atom of an aromatic hydrocarbon nucleus is substituted with a hydroxyl group. In the present invention, such a compound is merely referred to as "a phenol". Such phenols are referred to as monohydric phenols, dihydric phenols, trihydric phenols and so on in accordance with the number of hydroxyl groups, with dihydric and higher phenols being referred to as polyhydric phenols or polyphenols. Examples of monohydric phenols include phenol (hydroxybenzene), cresol, thymol, and carvacrol. Examples of dihydric phenols include catechol, resorcinol, hydroquinone, orcinol, and urushiol. Examples of trihydric phenols include pyrogallol, phloroglucinol, and hydroxyhydroquinone.

Other examples of phenols include dihydric bisphenol A which has two benzene nuclei, monohydric naphthol and dihydric binaphthol which have a naphthalene nucleus, and anthrol and anthrahydroquinone which have an anthracene nucleus. Phenol is in general also called carbolic acid, which corresponds to hydroxybenzene, and is a representative example of the phenol. Cresol has three isomers, ortho-cresol, meta-cresol and para-cresol, depending on the positional relationship between the hydroxyl group and the methyl group. Naphthol has two isomers, 1-naphthol and 2-naphthol, depending on the site of substitution of the hydroxyl group. The phenols listed above can be effectively used in the present invention, but there is no limitation to these phenols.

Phenol hydrogenation products are obtained upon hydrogenating the phenol. Examples of the phenol hydrogenation products are cyclohexanone derivatives and cyclohexanol derivatives. A phenol hydrogenation product that has not been completely hydrogenated but rather has a double bond or a CO bond remaining therein can be used as the raw material in the present invention, for example cyclohexanone can be used as the raw material, whereupon cyclohexanol is obtained through the hydrogenation. Examples of cyclohexanone derivatives include cyclohexanone, meta-methylcyclohexanone, ortho-methylcyclohexanone, para-methylcyclohexanone, tetralone, and decalone. Moreover, examples of cyclohexanol derivatives include cyclohexanol, meta-methylcyclohexanol, ortho-methylcyclohexanol, para-methylcyclohexanol, 1,2,3,4-tetrahydronaphthol, 5,6,7,8-tetrahydronaphthol, and decahydronaphthol.

As a specific example of the method of hydrogenating a phenol according to the present invention, for example in the case of hydrogenating phenol, the reaction formulae for synthesizing cyclohexanone and cyclohexanol through the hydrogenation of phenol are shown below in formulae (1) and (2).

Formula 1

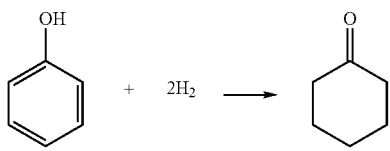

(1)

Formula 2

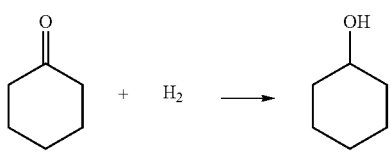

(1)

In the method of hydrogenating a phenol of the present invention, as shown in formula (1) above, partial hydrogenation in which four hydrogen atoms are added to the benzene nucleus of each phenol molecule proceeds, whereby cyclohexanone is synthesized. Then, as shown in formula (2) above, if two hydrogen atoms are added to each cyclohexanone molecule, then the hydrogenation is completed, whereby cyclohexanol is obtained. It is thought that the hydrogenation of phenol proceeds through successive reactions, with cyclohexanone being produced initially, and then the cyclohexanone being hydrogenated to synthesize cyclohexanol.

Cyclohexanone is used as a raw material of 6-nylon, and cyclohexanol is used as a raw material of 66-nylon, and hence it is important to be able to synthesize each selectively in accordance with the purpose. Development of a catalyst for this has been awaited.

In the phenol hydrogenation of the present invention, a supported rhodium and/or ruthenium catalyst can be suitably used as the catalyst. So long as the catalyst contains at least one metal selected from rhodium and ruthenium, the catalyst can be effectively used in the present invention. A catalyst prepared by adding at least one metallic element selected from the platinum group metals Pd, Os, Ir and Pt, metallic elements such as Ni, Co, Fe, Zn, Cu, Mn, Pb, Cd, Cr, Ag, Au, Hg, Ga, In, Ge, Sn, Ti, Al and Si, the group 2A elements Ca, Mg, Sr and Ba, and the alkali metals Li, Na, K, Rb and Cs to the rhodium and/or ruthenium or alloying therewith can also be effectively used in the present invention.

In the present invention, for example, activated charcoal, alumina, magnesia, silica, silica alumina, zirconia, titania, zeolite, clay, kaolin, talc, bentonite, or a gel or sol thereof can be suitably used as a carrier in the supported rhodium and/or ruthenium catalyst. A mixture of suitable ones of these carriers may also be used in the catalyst. The carrier is used with objectives such as dispersing catalytically active points of the metal or the like over the surface of the carrier so as to form a high-surface-area catalyst, and increasing the mechanical strength of the catalyst. There are no particular limitations on the carrier, so long as the carrier does not hamper the reaction or the catalytic activity; even a carrier that exhibits some degree of catalytic activity toward the reaction can be used.

Before use, the catalyst used in the present invention is preferably activated by being subjected to heating treatment in a stream of a gas such as hydrogen, nitrogen, argon, carbon dioxide, oxygen or air. The treatment temperature during the heating treatment is generally in a range of 50 to 700° C., preferably 80 to 600° C., more preferably 80 to 500° C., most preferably 100 to 500° C. A treatment temperature less than 50° C. is undesirable, since adsorbed matter will not be desorbed sufficiently. Moreover, a treatment temperature exceeding 700° C. is undesirable, since the structure of the carrier in the catalyst will become liable to break up, and hence the surface area will tend to drop, and moreover agglomeration of the metal particles will occur. The activation treatment time is influenced by the amount of matter adsorbed on the surface and the treatment temperature, and hence there are no particular limitations on this treatment time, although a treatment time of 0.1 to 100 hours is generally suitable.

Next, embodiments of the present invention will be described. The reaction method when carrying out the present invention may be any of a batch method, a semi-batch method or a continuous flow method. With the catalyst being in a solid state, the form of reaction may be any of liquid phase, vapor phase, liquid-vapor mixed phase, solid phase, or supercritical fluid phase, or any combination of these may be used. For example, with the catalyst being in a solid state, the reaction may be carried out in any form out of liquid-vapor mixed phase, solid-liquid-vapor mixed phase, liquid-supercritical fluid mixed phase or supercritical fluid phase. Furthermore, the reaction may be carried out under normal pressure or under a pressurized state. From the viewpoint of the reaction efficiency, using supercritical carbon dioxide is recommended, but the present invention is not limited thereto.

So long as the reaction temperature is not less than 20° C., there are no particular limitations thereon; a preferable reaction temperature range is 20 to 250° C., a more preferable reaction temperature range is 30 to 200° C., a yet more preferable reaction temperature range is 35 to 150° C., and a most preferably reaction temperature range is 35 to 120° C. If the reaction temperature is too low, then the reaction rate will drop and hence the manufacturing method will not be efficient, whereas if the reaction temperature is excessively high, then the cost of the reaction apparatus and the running cost will increase, and the selectivity and yield for the desired product may drop, and hence the method will not be economical.

In the present invention, hydrogen and carbon dioxide are used in the reaction. A generally used reaction pressure range is 0.1 to 150 MPa, a preferable reaction pressure range is 0.2 to 100 MPa, a more preferable reaction pressure range is 2 to 60 MPa, a yet more preferable reaction pressure range is 2 to 50 MPa, and a most preferable reaction pressure range is 10.4 to 45 MPa.

Furthermore, when carrying out the present invention, for example when carrying out a batch reaction, there are no particular limitations on the reaction time, but this time is preferably in a range of 1 minute to 20 hours, more preferably 1 minute to 10 hours, yet more preferably 3 minutes to 5 hours, most preferably 5 minutes to 3.5 hours.

When carrying out the hydrogenation, there are no particular limitations on the composition charged in of the hydrogen and the phenol that constitute the raw materials; for example, in the case of hydrogenating phenol, to attain a high conversion ratio, it is preferable to make the molar ratio of hydrogen to phenol high (the theoretical equivalent amount for partial hydrogenation is 2 equivalent of hydrogen relative to phenol, and the theoretical equivalent amount for complete hydrogenation is 3 equivalents of hydrogen relative to phenol). In the present invention, the molar ratio of the hydrogen to the phenol is generally in a range of 0.1 to 1000, preferably 1 to 500, more preferably 2 to 200, yet more preferably 2 to 100, most preferably 2 to 50. There is of course no limitation to these ranges in the present invention.

There will be no problems so long as the temperature of the hydrogen used in the hydrogenation in the present invention is not less than 20° C. and the pressure of the hydrogen is not less than 0.1 MPa. A preferable temperature range is 20 to 250° C., a more preferable temperature range is 30 to 200° C., a yet more preferable temperature range is 35 to 150° C., and a most preferable temperature range is 35 to 120° C. Moreover, a preferable pressure range for the hydrogen is 0.1 to 50 MPa, a more preferable pressure range is 1 to 30 MPa, a yet more preferable pressure range is 1 to 25 MPa, and a most preferable pressure range is 3 to 20 MPa.

There will be no problems so long as the temperature of the carbon dioxide that is made to participate in the hydrogenation in the present invention is not less than 20° C. and the pressure of the carbon dioxide is not less than 0.1 MPa. A preferable temperature range for the carbon dioxide is 20 to 250° C., a more preferable temperature range is 30 to 200° C., a yet more preferable temperature range is 35 to 150° C., and a most preferable temperature range is 35 to 120° C. Moreover, a preferable pressure range for the carbon dioxide is 0.1 to 50 MPa, a more preferable pressure range is 1 to 30 MPa, a yet more preferable pressure range is 1 to 25 MPa, and a most preferable pressure range is 7.4 to 25 MPa. In the present invention, when charging in the phenol and the hydrogen, carbon dioxide is introduced in and made to participate in the reaction; in this case, it is not necessary in particular to use a solvent. However, the phenol may be charged in after having been diluted using a solvent such as benzene, toluene, xylene, hexane, an alcohol, a ketone, or water.

In the present invention, there are no particular limitations on the amount of the catalyst used, but, for example, in the case of carrying out the present invention using a batch reaction, the amount of the catalyst used relative to the phenol that acts as the raw material may be in a range of 0.01 to 200 wt %, preferably 0.05 to 100 wt %, more preferably 0.05 to 50 wt %, yet more preferably 0.1 to 30 wt %, most preferably 0.1 to 10 wt %. The amount of the catalyst is set as appropriate in accordance with the reaction method, the reaction conditions, the types of the raw material and the catalyst, and so on, but if the amount of the catalyst used is too low, then there will be a substantial drop in the progress of the reaction, and if the amount of the catalyst used is too high, then problems may arise such as the efficiency of contact and so on dropping, and the manufacturing cost increasing.

After the present invention has been carried out, the products are in general contained together with unreacted raw material and so on in the mixed solution obtained after releasing the hydrogen and carbon dioxide, but a desired compound can be isolated and purified using a separation/purification method such as ordinary distillation, extraction, crystallization or column separation. For example, after the reaction has been completed, the obtained products are subjected together with unreacted raw material to extraction with methanol, and then the products are identified and subjected to quantitative analysis using a gas chromatograph-mass spectrometer, a liquid chromatograph measuring apparatus, a gas chromatograph measuring apparatus, an NMR measuring apparatus, or the like, whereby data on the conversion ratio and selectivity for the hydrogenation can be investigated. Moreover, in the case that the products are solid, the products can be separated from the catalyst through solvent extraction using acetone or the like, and then analyzed using a technique as above.

In the present invention, for example cyclohexanone and cyclohexanol are obtained through the hydrogenation of phenol. Taking this reaction as an example, a description will now be given of how the operating conditions affect the conversion ratio and the selectivities. It has been found that as the reaction temperature is increased between 50 and 110° C., the conversion ratio of the phenol increases, and the selectivity for cyclohexanone increases gradually. For example, under reaction conditions of a reaction time of 10 minutes, a hydrogen pressure of 3 MPa and a carbon dioxide pressure of 10 MPa, as the reaction temperature was increased between 50 and 110° C., the conversion ratio increased between 16 and 69%, and the selectivity for cyclohexanone increased between 58 and 75%.

Moreover, as the reaction time is increased, the conversion ratio of the phenol increases. For example, under reaction conditions of a reaction temperature of 80° C., a hydrogen pressure of 3 MPa and a carbon dioxide pressure of 10 MPa, as the reaction time was increased between 10 and 180 minutes, the conversion ratio increased between 35 and 91%. However, it was found that the selectivity for cyclohexanone was constant at approximately 67%. On the other hand, in the case that the hydrogen pressure was high at 9 MPa, under reaction conditions of a reaction temperature of 80° C. and a carbon dioxide pressure of 10 MPa, the reaction proceeded rapidly, with the conversion ratio reaching 70 to 99% in 10 to 30 minutes, but no large change was observed in the selectivity for cyclohexanone, which was 59 to 55%. With a reaction time of 60 minutes, the conversion ratio reached 100%, and the selectivity for cyclohexanone dropped to 22%, and hence it was found that the proportion of cyclohexanol increased rapidly. Considering these results, it is inferred that in the present invention, while phenol is present, hydrogenation of cyclohexanone hardly proceeds, and hence even if the reaction time is increased, the conversion ratio merely increases, but the selectivity for cyclohexanone does not change. It is thought that once the conversion ratio reaches 100% and hence there is no longer any phenol in the reaction system, hydrogenation of cyclohexanone proceeds and hence the proportion of cyclohexanol increases rapidly and progressively. Furthermore, as the amount of the catalyst is increased, the selectivity for cyclohexanol increases. The reaction conditions that are technically and economically optimal can thus be selected by changing the reaction temperature, the reaction time, the amount of the catalyst, and so on.

Moreover, in the case of keeping the hydrogen pressure constant and changing the carbon dioxide pressure, as the carbon dioxide pressure is increased, the conversion ratio of the phenol increases, and the selectivity for cyclohexanone drops. For example, under conditions of a reaction temperature of 80° C. and a reaction time of 10 minutes, in the case of keeping the hydrogen pressure constant at 3 MPa, as the carbon dioxide pressure was increased between 0.1 and 25.3 MPa, the conversion ratio increased slightly, but the selectivity for cyclohexanone dropped between 76 and 63%.

In the case of keeping the carbon dioxide pressure constant and increasing the hydrogen pressure, there is a tendency that the conversion ratio of the phenol increases, and the selectivity for cyclohexanol drops. For example, under conditions of a reaction temperature of 80° C. and a reaction time of 10 minutes, in the case of keeping the carbon dioxide pressure constant at 10 MPa, as the hydrogen pressure was increased between 1 and 9 MPa, the conversion ratio increased between 14 and 70%, but the selectivity for cyclohexanone dropped between 76 and 59%. In this way, in the present invention, the conversion ratio for the phenol hydrogenation and the selectivities for cyclohexanone and cyclohexanol can be adjusted by changing the carbon dioxide pressure and the hydrogen pressure.

In the case of hydrogenating phenol through a phenol hydrogenation process of prior art, for example by using an alumina-supported palladium catalyst, and introducing a mixed solution of phenol and cyclohexane with a phenol/cyclohexane molar ratio of ½ at a phenol flow rate of 0.0135 mol/hr into a hydrogen gas stream (hydrogen/phenol molar ratio=5.4) and carrying out reaction at 230° C., at the start of the flow reaction 98% cyclohexanone and 2% cyclohexanol were produced at a phenol conversion ratio of 77%. However, with this method, there is a drawback that a drop in activity and hence a drop in the conversion ratio occurs due to carbonaceous matter accumulating on the catalyst, and hence the conversion ratio became 63% thirty minutes after the start of the reaction, 55% after 1 hour, 44% after 2 hours, and 42% after 8 hours. Moreover, with this method, experimental operation using only phenol was difficult, and hence the phenol had to be used with harmful cyclohexane as a solvent (N. Mahata and V. Vishwanathan, Journal of Catalysis, 196, 262-270 (2000)).

In contrast with this, according to the method of hydrogenating a phenol of the present invention, hydrogenation of a phenol can be carried out at a lower reaction temperature than with the prior art. Moreover, due to reducing the reaction temperature, a drop in activity of the catalyst can be prevented. Furthermore by applying a novel rhodium and/or ruthenium supported metal catalyst to the hydrogenation of the phenol, the phenol hydrogenation can be made highly efficient. The present invention is thus useful in providing a novel phenol hydrogenation process that resolves the problems of the prior art.

Effects of the Invention

The present invention relates to a method of hydrogenating a phenol, and the following remarkable effects are produced through the present invention: (1) in the case of phenol hydrogenation in which carbon dioxide is made to participate in the reaction, by using a catalyst having rhodium and/or ruthenium supported thereon, the reaction temperature can be made lower than with prior art, and hence a drop in activity of the catalyst can be prevented; (2) an environmentally friendly phenol hydrogenation process that uses no harmful organic solvents can be provided; (3) a novel supported metal catalyst is applied to the phenol hydrogenation, whereby the phenol hydrogenation process can be made highly efficient, and the cost can be reduced; (4) because the catalyst used in the reaction is solid, in the case that the products are liquid, the catalyst can be easily separated from the products, and then purification can be carried out through distillation, solvent extraction or the like; and (5) industrially important phenol hydrogenation can be carried out efficiently using an environmentally friendly process.

BEST MODE FOR CARRYING OUT THE INVENTION

Following is a concrete description of the present invention through Examples. However, the present Examples merely describe suitable examples of the present invention, and the present invention is not limited to only these Examples.

EXAMPLE 1

0.02 mol of phenol and 0.0228 g of an activated charcoal-supported rhodium catalyst (amount of metal supported 5%, made by Wako Chemicals) were put into a stainless steel high-pressure reactor of internal volume 50 ml, a pressure of 10 MPa of hydrogen and a pressure of 10 MPa of carbon dioxide were introduced in, and hydrogenation was carried out for 2 hours at a reaction temperature of 80° C. After reaction had been completed, the hydrogen and carbon dioxide were released, and the products obtained were recovered by methanol extraction, and then analyzed using a gas chromatograph. The results were that the phenol conversion ratio was 100%, and the selectivities were 87% for cyclohexanol and 13% for cyclohexanone.

EXAMPLE 2

Products were obtained by carrying out reaction as in Example 1. However, the amount of the catalyst was changed to 0.0749 g. The reaction conditions were as follows.
(Reaction Conditions)
Substrate: 0.02 mol of phenol
Hydrogen pressure: 10 MPa
Carbon dioxide pressure: 10 MPa
Catalyst: 0.0749 g of activated charcoal-supported rhodium catalyst (amount of metal supported 5%, made by Wako Chemicals)
Reaction temperature: 80° C.
Reaction time: 2 hours The products obtained were analyzed using a gas chromatograph. The results were that the phenol conversion ratio was 100%, and the selectivities were 99% for cyclohexanol and 1% for cyclohexanone.

EXAMPLE 3

Products were obtained by carrying out reaction as in Example 1. However, the reaction time was changed to 20 minutes. The reaction conditions were as follows.
(Reaction Conditions)
Substrate: 0.02 mol of phenol
Hydrogen pressure: 10 MPa
Carbon dioxide pressure: 10 MPa
Catalyst: 0.0228 g of activated charcoal-supported rhodium catalyst (amount of metal supported 5%, made by Wako Chemicals)
Reaction temperature: 80° C.
Reaction time: 20 minutes The products obtained were analyzed using a gas chromatograph. The results were that the phenol conversion ratio was 49%, and the selectivities were 50% for cyclohexanol and 50% for cyclohexanone.

EXAMPLE 4

Products were obtained by carrying out reaction as in Example 1. However, the reaction temperature was changed to 55° C. The reaction conditions were as follows.
(Reaction Conditions)
Substrate: 0.02 mol of phenol
Hydrogen pressure: 10 MPa Carbon dioxide pressure: 10 MPa
Catalyst: 0.0228 g of activated charcoal-supported rhodium catalyst (amount of metal supported 5%, made by Wako Chemicals)
Reaction temperature: 55° C.
Reaction time: 2 hours The products obtained were analyzed using a gas chromatograph. The results were that the phenol conversion ratio was 53%, and the selectivities were 83% for cyclohexanol and 17% for cyclohexanone.

EXAMPLE 5

Products were obtained by carrying out reaction as in Example 1. However, the reaction temperature was changed to 45° C. The reaction conditions were as follows.
(Reaction Conditions)
Substrate: 0.02 mol of phenol
Hydrogen pressure: 10 MPa
Carbon dioxide pressure: 10 MPa
Catalyst: 0.0228 g of activated charcoal-supported rhodium catalyst (amount of metal supported 5%, made by Wako Chemicals)
Reaction temperature: 45° C.
Reaction time: 2 hours The products obtained were analyzed using a gas chromatograph. The results were that the phenol conversion ratio was 35.4%, and the selectivities were 66% for cyclohexanol and 34% for cyclohexanone.

EXAMPLE 6

Products were obtained by carrying out reaction as in Example 1. However, the reaction temperature was changed to 55° C. and the carbon dioxide pressure was changed to 20 MPa. The reaction conditions were as follows.
(Reaction Conditions)
Substrate: 0.02 mol of phenol
Hydrogen pressure: 10 MPa
Carbon dioxide pressure: 20 MPa
Catalyst: 0.0228 g of activated charcoal-supported rhodium catalyst (amount of metal supported 5%, made by Wako Chemicals)
Reaction temperature: 55° C.
Reaction time: 2 hours The products obtained were analyzed using a gas chromatograph. The results were that the phenol conversion ratio was 87%, and the selectivities were 65% for cyclohexanol and 35% for cyclohexanone.

EXAMPLE 7

Products were obtained by carrying out reaction as in Example 1. However, the reaction temperature was changed to 55° C. and the hydrogen pressure was changed to 6 MPa. The reaction conditions were as follows.
(Reaction Conditions)
Substrate: 0.02 mol of phenol
Hydrogen pressure: 6 MPa
Carbon dioxide pressure: 10 MPa
Catalyst: 0.0228 g of activated charcoal-supported rhodium catalyst (amount of metal supported 5%, made by Wako Chemicals)
Reaction temperature: 55° C.
Reaction time: 2 hours The products obtained were analyzed using a gas chromatograph. The results were that the phenol conversion ratio was 39%, and the selectivities were 60% for cyclohexanol and 40% for cyclohexanone.

EXAMPLE 8

Products were obtained by carrying out reaction as in Example 1. However, to study the possibility of reusing the catalyst, the same catalyst was reused and a study was carried out into any change in the conversion ratio or the selectivities. The reaction conditions were as follows.
(Reaction Conditions)
Substrate: 0.02 mol of phenol
Hydrogen pressure: 10 MPa
Carbon dioxide pressure: 10 MPa
Catalyst: 0.0228 g of activated charcoal-supported rhodium catalyst (amount of metal supported 5%, made by Wako Chemicals)
Reaction temperature: 80° C.
Reaction time: 2 hours The test results are shown in the table below. The catalyst was reused 10 times, and during these tests, there was hardly any change in the phenol conversion ratio or the selectivities for cyclohexanol and cyclohexanone; loss of catalyst activity was thus not observed.

| | Test results | |
|---|---|---|
| | Phenol conversion | Selectivity (%) |
| Test no. | ratio (%) | Cyclohexanol | Cyclohexanone |
| 1st | 100 | 87 | 13 |
| 2nd | 100 | 87 | 13 |
| 3rd | 100 | 88 | 12 |
| 5th | 100 | 87 | 13 |
| 10th | 100 | 88 | 12 |

EXAMPLE 9

Products were obtained by carrying out reaction as in Example 1. However, the reaction temperature was changed to 55° C. and the catalyst was changed to 0.0639 g of an activated charcoal-supported ruthenium catalyst (amount of metal supported 5%, made by Wako Chemicals). The reaction conditions were as follows.
(Reaction Conditions)
Substrate: 0.02 mol of phenol
Hydrogen pressure: 10 MPa
Carbon dioxide pressure: 10 MPa
Catalyst: 0.0639 g of activated charcoal-supported ruthenium catalyst (amount of metal supported 5%, made by Wako Chemicals)
Reaction temperature: 55° C.
Reaction time: 2 hours The products obtained were analyzed using a gas chromatograph. The results were that the phenol conversion ratio was 30%, and the selectivities were 95% for cyclohexanol and 5% for cyclohexanone.

COMPARATIVE EXAMPLE 1

Products were obtained by carrying out reaction as in Example 4. However, the catalyst was changed to 0.0467 g of an activated charcoal-supported palladium catalyst (amount of metal supported 5%, made by Wako Chemicals).
The reaction conditions were as follows.
(Reaction Conditions)
Substrate: 0.02 mol of phenol
Hydrogen pressure: 10 MPa
Carbon dioxide pressure: 10 MPa
Catalyst: 0.0467 g of activated charcoal-supported palladium catalyst (amount of metal supported 5%, made by Wako Chemicals)
Reaction temperature: 55° C.
Reaction time: 2 hours The products obtained were analyzed using a gas chromatograph. The results were that the phenol conversion ratio was 1%, and the selectivities were 46% for cyclohexanol and 54% for cyclohexanone.

COMPARATIVE EXAMPLE 2

Products were obtained by carrying out reaction as in Example 1. However, the catalyst was changed to 0.0780 g of an activated charcoal-supported platinum catalyst (amount of metal supported 5%, made by Wako Chemicals). The reaction conditions were as follows.
(Reaction Conditions)
Substrate: 0.02 mol of phenol
Hydrogen pressure: 10 MPa
Carbon dioxide pressure: 10 MPa
Catalyst: 0.0780 g of activated charcoal-supported platinum catalyst (amount of metal supported 5%, made by Wako Chemicals)
Reaction temperature: 80° C.
Reaction time: 2 hours The products obtained were analyzed using a gas chromatograph. The results were that the phenol conversion ratio was 1%, and the selectivities were 3% for cyclohexanol and 97% for cyclohexanone.

EXAMPLE 10

0.0185 mol of meta-cresol and 0.0455 g of an activated charcoal-supported rhodium catalyst (amount of metal supported 5%, made by Wako Chemicals) were put into a stainless steel high-pressure reactor of internal volume 50 ml, 9 MPa of hydrogen and 11 MPa of carbon dioxide were introduced in, and hydrogenation was carried out for 2 hours at a reaction temperature of 55° C. After reaction had been completed, the hydrogen and carbon dioxide were released, and the organic matter obtained was recovered by methanol extraction, and then analyzed using a gas chromatograph. The results were that the meta-cresol conversion ratio was 99%, and the selectivities were 17% for meta-methylcyclohexanol and 83% for meta-methylcyclohexanone.

EXAMPLE 11

Products were obtained by carrying out reaction as in Example 10. However, the substrate was changed to 0.0185 mol of ortho-cresol. The reaction conditions were as follows.
(Reaction Conditions)
Substrate: 0.0185 mol of ortho-cresol
Hydrogen pressure: 9 MPa
Carbon dioxide pressure: 11 MPa
Catalyst: 0.0455 g of activated charcoal-supported rhodium catalyst (amount of metal supported 5%, made by Wako Chemicals)
Reaction temperature: 55° C.
Reaction time: 2 hours The products obtained were analyzed using a gas chromatograph. The results were that the ortho-cresol conversion ratio was 88%, and the selectivities were 69% for ortho-methylcyclohexanol and 31% for ortho-methylcyclohexanone.

EXAMPLE 12

Products were obtained by carrying out reaction as in Example 10. However, the substrate was changed to 0.0185 mol of para-cresol. The reaction conditions were as follows.
(Reaction Conditions)
Substrate: 0.0185 mol of para-cresol
Hydrogen pressure: 9 MPa
Carbon dioxide pressure: 11 MPa
Catalyst: 0.0455 g of activated charcoal-supported rhodium catalyst (amount of metal supported 5%, made by Wako Chemicals)
Reaction temperature: 55° C.
Reaction time: 2 hours The products obtained were analyzed using a gas chromatograph. The results were that the para-cresol conversion ratio was 47%, and the selectivities were 45% for para-methylcyclohexanol and 55% for para-methylcyclohexanone.

EXAMPLE 13

0.2014 g of 1-naphthol and 0.0205 g of an activated charcoal-supported rhodium catalyst (amount of metal supported 5%, made by Wako Chemicals) were put into a stainless steel high-pressure reactor of internal volume 50 ml, a pressure of 3.0 MPa of hydrogen and a pressure of 16 MPa of carbon dioxide were introduced in, and hydrogenation was carried out for 45 minutes at a reaction temperature of 50° C. After reaction had been completed, the hydrogen and carbon dioxide were released, and the products obtained were recovered by acetone extraction, and then analyzed using a gas chromatograph-mass spectrometer. The 1-naphthol conversion ratio was 79.5%, and the selectivities were 72.8% for 5,6,7,8-tetrahydronaphthol, 11.5% for 1,2,3,4-tetrahydronaphthol and 4.6% for tetralone, the selectivity for hydrogenation being 98.6%. Moreover, the selectivities were 0.9% for tetralin and 0.5% for decalin, which are byproducts, and hence it is thought that the selectivity for dehydration of the 1-naphthol was 1.4%.

EXAMPLE 14

Products were obtained by carrying out reaction as in Example 1. However, the hydrogen pressure was changed to 3 MPa and the reaction time was changed to 10 minutes. The reaction conditions were as follows.
(Reaction Conditions)
Substrate: 0.02 mol of phenol
Hydrogen pressure: 3 MPa
Carbon dioxide pressure: 10.1 MPa
Catalyst: 0.0203 g of activated charcoal-supported rhodium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 35%, and the selectivities were 68% for cyclohexanone and 32% for cyclohexanol.

EXAMPLE 15

Products were obtained by carrying out reaction as in Example 14. However, the catalyst was changed to an activated charcoal-supported ruthenium catalyst. The reaction conditions were as follows.
(Reaction Conditions)
Substrate: 0.02 mol of phenol
Hydrogen pressure: 3 MPa
Carbon dioxide pressure: 10.1 MPa
Catalyst: 0.0206 g of activated charcoal-supported ruthenium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 11%, and the selectivities were 69% for cyclohexanone and 31% for cyclohexanol.

COMPARATIVE EXAMPLE 3

Products were obtained by carrying out reaction as in Example 14. However, the catalyst was changed to an activated charcoal-supported palladium catalyst. The reaction conditions were as follows.
(Reaction Conditions)
Substrate: 0.02 mol of phenol
Hydrogen pressure: 3 MPa
Carbon dioxide pressure: 10.1 MPa
Catalyst: 0.0196 g of activated charcoal-supported palladium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 1%, and the selectivities were 91% for cyclohexanone and 9% for cyclohexanol.

COMPARATIVE EXAMPLE 4

Products were obtained by carrying out reaction as in Example 14. However, the catalyst was changed to an alumina-supported platinum catalyst. The reaction conditions were as follows.
(Reaction Conditions)
Substrate: 0.02 mol of phenol
Hydrogen pressure: 3.1 MPa
Carbon dioxide pressure: 10 MPa
Catalyst: 0.0204 g of alumina-supported platinum catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 1%, and the selectivities were 72% for cyclohexanone and 28% for cyclohexanol.

EXAMPLE 16

Products were obtained by carrying out reaction as in Example 14. However, the reaction temperature was changed to 70° C. The reaction conditions were as follows.
(Reaction Conditions)
Substrate: 0.02 mol of phenol
Hydrogen pressure: 3 MPa
Carbon dioxide pressure: 10.1 MPa
Catalyst: 0.0192 g of activated charcoal-supported rhodium catalyst (amount of metal supported 5%, made by Wako Chemicals)
Reaction temperature: 70° C.
Reaction time: 10 minutes The products obtained were analyzed using a gas chromatograph. The results were that the phenol conversion ratio was 28%, and the selectivities were 64% for cyclohexanone and 36% for cyclohexanol.

EXAMPLE 17

Products were obtained by carrying out reaction as in Example 14. However, the reaction temperature was changed to 60° C. The reaction conditions were as follows.
(Reaction Conditions)
Substrate: 0.02 mol of phenol
Hydrogen pressure: 3 MPa
Carbon dioxide pressure: 10 MPa
Catalyst: 0.0201 g of activated charcoal-supported rhodium catalyst (amount of metal supported 5%, made by Wako Chemicals)
Reaction temperature: 60° C.
Reaction time: 10 minutes The products obtained were analyzed using a gas chromatograph. The results were that the phenol conversion ratio was 20%, and the selectivities were 61% for cyclohexanone and 39% for cyclohexanol.

EXAMPLE 18

Products were obtained by carrying out reaction as in Example 14. However, the reaction temperature was changed to 50° C. The reaction conditions were as follows.
(Reaction Conditions)
Substrate: 0.02 mol of phenol
Hydrogen pressure: 3.1 MPa
Carbon dioxide pressure: 9.9 MPa
Catalyst: 0.0202 g of activated charcoal-supported rhodium catalyst (amount of metal supported 5%, made by Wako Chemicals)
Reaction temperature: 50° C.
Reaction time: 10 minutes The products obtained were analyzed using a gas chromatograph. The results were that the phenol conversion ratio was 16%, and the selectivities were 58% for cyclohexanone and 42% for cyclohexanol.

EXAMPLE 19

Products were obtained by carrying out reaction as in Example 14. However, the reaction temperature was changed to 110° C. The reaction conditions were as follows.
(Reaction Conditions)
Substrate: 0.02 mol of phenol
Hydrogen pressure: 3 MPa
Carbon dioxide pressure: 10.2 MPa Catalyst: 0.0202 g of activated charcoal-supported rhodium catalyst (amount of metal supported 5%, made by Wako Chemicals)
Reaction temperature: 110° C.
Reaction time: 10 minutes The products obtained were analyzed using a gas chromatograph. The results were that the phenol conversion ratio was 69%, and the selectivities were 75% for cyclohexanone and 25% for cyclohexanol.

The relationships between the phenol hydrogenation conditions and the conversion ratio and product selectivities for Examples 14, 16, 17, 18 and 19 are shown in Table 1. Under reaction conditions of a reaction time of 10 minutes, a hydrogen pressure of 3 MPa and a carbon dioxide pressure of 10 MPa, as the reaction temperature was increased between 50 and 110° C., the conversion ratio increased between 16 and 69%, and the selectivity for cyclohexanone increased between 58 and 75%.

TABLE 1

| Sample | Reaction temperature (° C.) | Conversion ratio (%) | Cyclohexanone selectivity (%) | Cyclohexanol selectivity (%) |
|---|---|---|---|---|
| Example 18 | 50 | 16 | 58 | 42 |
| Example 17 | 60 | 20 | 61 | 39 |
| Example 16 | 70 | 28 | 64 | 36 |
| Example 14 | 80 | 35 | 68 | 32 |
| Example 19 | 110 | 69 | 75 | 25 |

Substrate: phenol, hydrogen pressure: 3 MPa, carbon dioxide pressure: 10 MPa, activated charcoal-supported rhodium catalyst, reaction time: 10 minutes

EXAMPLE 20

Products were obtained by carrying out reaction as in Example 14. However, the hydrogen pressure was changed to 1 MPa. The reaction conditions were as follows.
(Reaction Conditions)
Substrate: 0.02 mol of phenol
Hydrogen pressure: 1 MPa
Carbon dioxide pressure: 10 MPa
Catalyst: 0.0203 g of activated charcoal-supported rhodium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 14%, and the selectivities were 76% for cyclohexanone and 24% for cyclohexanol.

EXAMPLE 21

Products were obtained by carrying out reaction as in Example 14. However, the hydrogen pressure was changed to 6 MPa. The reaction conditions were as follows.
(Reaction Conditions)
Substrate: 0.02 mol of phenol
Hydrogen pressure: 6 MPa
Carbon dioxide pressure: 10.2 MPa
Catalyst: 0.0208 g of activated charcoal-supported rhodium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 57%, and the selectivities were 61% for cyclohexanone and 39% for cyclohexanol.

EXAMPLE 22

Products were obtained by carrying out reaction as in Example 14. However, the hydrogen pressure was changed to 9 MPa. The reaction conditions were as follows.
(Reaction Conditions)
Substrate: 0.02 mol of phenol
Hydrogen pressure: 9 MPa
Carbon dioxide pressure: 10.4 MPa
Catalyst: 0.0208 g of activated charcoal-supported rhodium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 70%, and the selectivities were 59% for cyclohexanone and 41% for cyclohexanol.

The relationships between the phenol hydrogenation conditions and the conversion ratio and product selectivities for Examples 14, 20, 21 and 22 are shown in Table 2. Under reaction conditions of a reaction temperature of 80° C., a reaction time of 10 minutes and a carbon dioxide pressure of 10 MPa, as the hydrogen pressure was increased between 1 and 9 MPa, the conversion ratio increased between 14 and 70%, but the selectivity for cyclohexanone dropped between 76 and 59%.

TABLE 2

| Sample | Hydrogen pressure (MPa) | Conversion ratio (%) | Cyclohexanone selectivity (%) | Cyclohexanol selectivity (%) |
|---|---|---|---|---|
| Example 20 | 1 | 14 | 76 | 24 |
| Example 14 | 3 | 35 | 68 | 32 |
| Example 21 | 6 | 57 | 61 | 39 |
| Example 22 | 9 | 70 | 59 | 41 |

Substrate: phenol, reaction temperature: 80° C., carbon dioxide pressure: 10 MPa, activated charcoal-supported rhodium catalyst, reaction time: 10 minutes

EXAMPLE 23

Products were obtained by carrying out reaction as in Example 14. However, the carbon dioxide pressure was changed to 0.1 MPa. The reaction conditions were as follows.
(Reaction Conditions)
Substrate: 0.02 mol of phenol
Hydrogen pressure: 3 MPa
Carbon dioxide pressure: 0.1 MPa
Catalyst: 0.0204 g of activated charcoal-supported rhodium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 37%, and the selectivities were 76% for cyclohexanone and 24% for cyclohexanol.

EXAMPLE 24

Products were obtained by carrying out reaction as in Example 14. However, the carbon dioxide pressure was changed to 25.3 MPa. The reaction conditions were as follows.
(Reaction Conditions)
Substrate: 0.02 mol of phenol
Hydrogen pressure: 3 MPa
Carbon dioxide pressure: 25.3 MPa
Catalyst: 0.0209 g of activated charcoal-supported rhodium catalyst (amount of metal supported 5%, made by Wako Chemicals)
Reaction temperature: 80° C.
Reaction time: 10 minutes The products obtained were analyzed using a gas chromatograph. The results were that the phenol conversion ratio was 44%, and the selectivities were 63% for cyclohexanone and 37% for cyclohexanol.

The relationships between the phenol hydrogenation conditions and the conversion ratio and product selectivities for Examples 14, 23 and 24 are shown in Table 3. Under reaction conditions of a reaction temperature of 80° C., a reaction time of 10 minutes and a hydrogen pressure of 3 MPa, as the carbon dioxide pressure was increased between 0.1 and 25.3 MPa, the conversion ratio increased slightly, but the selectivity for cyclohexanone dropped between 76 and 63%.

TABLE 3

| Sample | Carbon dioxide pressure (MPa) | Conversion ratio (%) | Cyclo-hexanone selectivity (%) | Cyclo-hexanol selectivity (%) |
|---|---|---|---|---|
| Example 23 | 0.1 | 37 | 76 | 24 |
| Example 14 | 10.1 | 35 | 68 | 32 |
| Example 24 | 25.3 | 44 | 63 | 37 |

Substrate: phenol, reaction temperature: 80° C., hydrogen pressure: 3 MPa, activated charcoal-supported rhodium catalyst, reaction time: 10 minutes

EXAMPLE 25

Products were obtained by carrying out reaction as in Example 14. However, the reaction time was changed to 30 minutes. The reaction conditions were as follows.
(Reaction Conditions)
Substrate: 0.02 mol of phenol
Hydrogen pressure: 3.1 MPa
Carbon dioxide pressure: 10.1 MPa
Catalyst: 0.0204 g of activated charcoal-supported rhodium catalyst (amount of metal supported 5%, made by Wako Chemicals)
Reaction temperature: 80° C.
Reaction time: 30 minutes The products obtained were analyzed using a gas chromatograph. The results were that the phenol conversion ratio was 55%, and the selectivities were 67% for cyclohexanone and 33% for cyclohexanol.

EXAMPLE 26

Products were obtained by carrying out reaction as in Example 14. However, the reaction time was changed to 60 minutes. The reaction conditions were as follows.
(Reaction Conditions)
Substrate: 0.02 mol of phenol
Hydrogen pressure: 3.1 MPa
Carbon dioxide pressure: 9.9 MPa
Catalyst: 0.0208 g of activated charcoal-supported rhodium catalyst (amount of metal supported 5%, made by Wako Chemicals)
Reaction temperature: 80° C.
Reaction time: 60 minutes The products obtained were analyzed using a gas chromatograph. The results were that the phenol conversion ratio was 75%, and the selectivities were 67% for cyclohexanone and 33% for cyclohexanol.

EXAMPLE 27

Products were obtained by carrying out reaction as in Example 14. However, the reaction time was changed to 180 minutes. The reaction conditions were as follows.
(Reaction Conditions)
Substrate: 0.02 mol of phenol
Hydrogen pressure: 3.1 MPa
Carbon dioxide pressure: 10 MPa
Catalyst: 0.0205 g of activated charcoal-supported rhodium catalyst (amount of metal supported 5%, made by Wako Chemicals)
Reaction temperature: 80° C.
Reaction time: 180 minutes The products obtained were analyzed using a gas chromatograph. The results were that the phenol conversion ratio was 91%, and the selectivities were 67% for cyclohexanone and 33% for cyclohexanol.

The relationships between the phenol hydrogenation conditions and the conversion ratio and product selectivities for Examples 14, 25, 26 and 27 are shown in Table 4. Under reaction conditions of a reaction temperature of 80° C., a hydrogen pressure of 3 MPa and a carbon dioxide pressure of 10 MPa, as the reaction time was increased between 10 and 180 minutes, the conversion ratio increased between 35 and 91%, but it was found that the selectivity for cyclohexanone was constant at approximately 67%.

TABLE 4

| Sample | Reaction time (min) | Conversion ratio (%) | Cyclo-hexanone selectivity (%) | Cyclo-hexanol selectivity (%) |
|---|---|---|---|---|
| Example 14 | 10 | 35 | 68 | 32 |
| Example 25 | 30 | 55 | 67 | 33 |
| Example 26 | 60 | 75 | 67 | 33 |
| Example 27 | 180 | 91 | 67 | 33 |

Substrate: phenol, hydrogen pressure: 3 MPa, carbon dioxide pressure: 10 MPa, activated charcoal-supported rhodium catalyst

EXAMPLE 28

Products were obtained by carrying out reaction as in Example 22. However, the reaction time was changed to 30 minutes. The reaction conditions were as follows.
(Reaction Conditions)
Substrate: 0.02 mol of phenol
Hydrogen pressure: 9 MPa
Carbon dioxide pressure: 10.3 MPa Catalyst: 0.0209 g of activated charcoal-supported rhodium catalyst (amount of metal supported 5%, made by Wako Chemicals)

Reaction temperature: 80° C.

Reaction time: 30 minutes

The products obtained were analyzed using a gas chromatograph. The results were that the phenol conversion ratio was 99%, and the selectivities were 55% for cyclohexanone and 45% for cyclohexanol.

EXAMPLE 29

Products were obtained by carrying out reaction as in Example 22. However, the reaction time was changed to 60 minutes. The reaction conditions were as follows.

(Reaction Conditions)

Substrate: 0.02 mol of phenol

Hydrogen pressure: 9 MPa

Carbon dioxide pressure: 10.3 MPa

Catalyst: 0.0206 g of activated charcoal-supported rhodium catalyst (amount of metal supported 5%, made by Wako Chemicals)

Reaction temperature: 80° C.

Reaction time: 60 minutes

The products obtained were analyzed using a gas chromatograph. The results were that the phenol conversion ratio was 100%, and the selectivities were 22% for cyclohexanone and 78% for cyclohexanol.

The relationships between the phenol hydrogenation conditions and the conversion ratio and product selectivities for Examples 22, 28 and 29 are shown in Table 5. Under reaction conditions of a reaction temperature of 80° C., a hydrogen pressure of 9 MPa and a carbon dioxide pressure of 10 MPa, reaction proceeded rapidly, with the conversion ratio reaching 70 to 99% in 10 to 30 minutes, but no large change was observed in the selectivity for cyclohexanone, which was 59 to 55%. With a reaction time of 60 minutes, the conversion ratio was 100%, and the selectivity for cyclohexanone was 22%. Considering together with the results in Table 4, it is inferred that in the present invention, while phenol is present, hydrogenation of cyclohexanone hardly proceeds, and hence even if the reaction time is increased, the conversion ratio merely increases, but the selectivity for cyclohexanone does not change. It is thought that once the conversion ratio reaches 100% and hence there is no longer any phenol in the reaction system, hydrogenation of cyclohexanone proceeds and hence the proportion of cyclohexanol increases rapidly and progressively.

TABLE 5

| Sample | Reaction time (min) | Conversion ratio (%) | Cyclo-hexanone selectivity (%) | Cyclo-hexanol selectivity (%) |
| --- | --- | --- | --- | --- |
| Example 22 | 10 | 70 | 59 | 41 |
| Example 28 | 30 | 99 | 55 | 45 |
| Example 29 | 60 | 100 | 22 | 78 |

Substrate: phenol, reaction temperature: 80° C., hydrogen pressure: 9 MPa, carbon dioxide pressure: 10 MPa, activated charcoal-supported rhodium catalyst

EXAMPLE 30

Products were obtained by carrying out reaction as in Example 23. However, the catalyst was changed to an alumina-supported rhodium catalyst. The reaction conditions were as follows.

(Reaction Conditions)

Substrate: 0.02 mol of phenol

Hydrogen pressure: 3 MPa

Carbon dioxide pressure: 0.1 MPa

Catalyst: 0.0202 g of alumina-supported rhodium catalyst (amount of metal supported 5%, made by Wako Chemicals)

Reaction temperature: 80° C.

Reaction time: 10 minutes

The products obtained were analyzed using a gas chromatograph. The results were that the phenol conversion ratio was 43%, and the selectivities were 88% for cyclohexanone and 12% for cyclohexanol.

EXAMPLE 31

Products were obtained by carrying out reaction as in Example 22. However, the phenol was changed to cyclohexanone. The reaction conditions were as follows.

(Reaction Conditions)

Substrate: 0.02 mol of cyclohexanone

Hydrogen pressure: 9 MPa

Carbon dioxide pressure: 10.1 MPa

Catalyst: 0.0203 g of activated charcoal-supported rhodium catalyst (amount of metal supported 5%, made by Wako Chemicals)

Reaction temperature: 80° C.

Reaction time: 10 minutes

The products obtained were analyzed using a gas chromatograph. The results were that the cyclohexanone conversion ratio was 100%, and the selectivity was 100% for cyclohexanol.

INDUSTRIAL APPLICABILITY

As described in detail above, the present invention relates to a method of hydrogenating a phenol, and according to the present invention, in the case of phenol hydrogenation in which carbon dioxide is made to participate in the reaction, by using a catalyst having rhodium and/or ruthenium supported thereon, the reaction temperature can be made lower than with prior art, and hence a drop in activity of the catalyst can be prevented. An environmentally friendly phenol hydrogenation process that uses no harmful organic solvents can be provided. By applying a novel supported metal catalyst to phenol hydrogenation, the phenol hydrogenation process can be made highly efficient, and the cost can be reduced. The catalyst used in the reaction is solid, and hence in the case that the products are liquid, the catalyst can be easily separated from the products, and then purification can be carried out through distillation, solvent extraction or the like. Industrially important phenol hydrogenation can be carried out efficiently using an environmentally friendly process.

The invention claimed is:

1. A method of hydrogenating a phenol using carbon dioxide, the method comprising reacting a phenol and hydrogen together in the presence of a supported rhodium and/or ruthenium catalyst, carbon dioxide, so as to hydrogenate the phenol.

2. The method of hydrogenating a phenol according to claim 1, wherein the hydrogenation is carried out at a reaction temperature of 20 to 250° C.

3. The method of hydrogenating a phenol according to claim 1, wherein the hydrogenation is carried out at a reaction pressure of 0.2 to 100 MPa.

4. The method of hydrogenating a phenol according to claim 1, wherein at least one type of supported catalyst selected from an activated charcoal-supported rhodium catalyst, an alumina-supported rhodium catalyst and an activated charcoal-supported ruthenium catalyst is used as the catalyst.

5. The method of hydrogenating a phenol according to claim 1, wherein carbon dioxide having a temperature of 20 to 250° C. and a pressure of 0.1 to 50 MPa is used as the carbon dioxide.

6. The method of hydrogenating a phenol according to claim 1, wherein hydrogen under conditions of a temperature of 20 to 250° C. and a pressure of 0.1 to 50 MPa is used.

7. The method of hydrogenating a phenol according to claim 1, wherein supercritical carbon dioxide is used as the carbon dioxide.

8. The method of hydrogenating a phenol according to claim 1, wherein the hydrogen pressure and the carbon dioxide pressure are adjusted in the presence of the phenol so as to control the conversion ratio of the phenol and/or the selectivities for the phenol hydrogenation products.

9. The method of hydrogenating a phenol according to claim 1, wherein the hydrogen pressure and the carbon dioxide pressure are adjusted in the absence of the phenol so as to hydrogenate a cyclohexanone derivative and control the selectivities for the phenol hydrogenation products.

10. The method of hydrogenating a phenol according to claim 1, wherein after the conversion ratio of the phenol has reached 100%, the hydrogen pressure and the carbon dioxide pressure are adjusted so as to control the selectivities for the phenol hydrogenation products.

11. The method of hydrogenating a phenol according to claim 1, wherein phenol or cresol is used as the phenol.

12. The method of hydrogenating a phenol according to claim 11, wherein cresol comprising at least one of meta-cresol, ortho-cresol and para-cresol is used as the cresol.

13. The method of hydrogenating a phenol according to claim 1, wherein naphthol is used as the phenol.

14. The method of hydrogenating a phenol according to claim 1, wherein each of the phenol hydrogenation products is a cyclohexanone derivative or a cyclohexanol derivative.

15. The method of hydrogenating a phenol according to claim 14, wherein the cyclohexanone derivative is cyclohexanone, meta-methylcyclohexanone, ortho-methylcyclohexanone, para-methylcyclohexanone or tetralone, and the cyclohexanol derivative is cyclohexanol, meta-methylcyclohexanol, ortho-methylcyclohexanol, para-methylcyclohexanol, 1,2,3,4-tetrahydronaphthol, 5,6,7,8-tetrahydronaphthol or decahydronaphthol.

16. The method of hydrogenating a phenol according to claim 1, which is carried out in the absence of a solvent.

* * * * *